US006183763B1

(12) United States Patent
Beerse et al.

(10) Patent No.: US 6,183,763 B1
(45) Date of Patent: *Feb. 6, 2001

(54) ANTIMICROBIAL WIPES WHICH PROVIDE IMPROVED IMMEDIATE GERM REDUCTION

(75) Inventors: Peter William Beerse, Maineville; Jeffrey Michael Morgan, Springboro; Kathleen Grieshop Baier, Cincinnati; Wei Cen, Cincinnati; Theresa Anne Bakken, Cincinnati, all of OH (US)

(73) Assignee: Procter & Gamble Company, Cincinnati, OH (US)

(*) Notice: Under 35 U.S.C. 154(b), the term of this patent shall be extended for 0 days.

This patent is subject to a terminal disclaimer.

(21) Appl. No.: 08/868,687

(22) Filed: Jun. 4, 1997

(51) Int. Cl.$^7$ .............................. A01N 25/34; A61K 7/50; A61K 7/40; A61K 7/48

(52) U.S. Cl. .................... 424/404; 510/130; 510/131; 510/138; 510/157

(58) Field of Search ............................................. 424/401

(56) References Cited

U.S. PATENT DOCUMENTS

| | | | |
|---|---|---|---|
| 2,999,265 | 9/1961 | Duane et al. | 424/16 |
| 3,057,467 | 10/1962 | Williams | 206/46 |
| 3,141,821 | 7/1964 | Compeau | 167/58 |

(List continued on next page.)

FOREIGN PATENT DOCUMENTS

| | | | |
|---|---|---|---|
| 0037224 A1 | 10/1981 | (EP) | C11D/3/48 |
| 0368146 | 5/1990 | (EP) | C11D/3/50 |
| 0403304 | 12/1990 | (EP) | A61K/7/06 |
| 0 613 675 | 9/1994 | (EP) | A61K/7/00 |
| 0619074 A1 | 10/1994 | (EP) | A01N/57/12 |
| 0670158 A2 | 9/1995 | (EP) | A61K/7/50 |
| 2288811 | 11/1995 | (GB) | C11D/1/831 |
| 2530661 | 6/1996 | (JP) | A61K/7/50 |
| WO 92/18100 | 4/1992 | (WO) | A61K/7/50 |
| WO 93/17588 | 9/1993 | (WO) | A23L/2/38 |
| WO 94/06440 | 9/1993 | (WO) | A61K/31/74 |
| WO 94/18292 | 8/1994 | (WO) | C11D/1/66 |
| WO 95/03028 | 2/1995 | (WO) | A61K/7/00 |
| WO 95/03781 | 3/1995 | (WO) | A61K/7/48 |
| WO 95/32705 | 5/1995 | (WO) | A61K/7/50 |
| WO 95/24179 | 9/1995 | (WO) | A61K/7/00 |
| WO 96/06152 | 2/1996 | (WO) | C11D/3/00 |
| WO 96/06153 | 2/1996 | (WO) | C11D/3/00 |
| WO 96/29049 | 2/1996 | (WO) | A61K/7/48 |
| WO 96/17918 | 6/1996 | (WO) | C11D/1/83 |
| WO 96/21426 | 7/1996 | (WO) | A61K/7/50 |
| WO 96/25913 | 8/1996 | (WO) | A61K/7/16 |
| WO 96/29983 | 10/1996 | (WO) | A61K/7/50 |
| WO 97/00676 | 1/1997 | (WO) | A61K/31/19 |
| WO 97/03647 | 2/1997 | (WO) | A61K/7/50 |
| WO 97/07781 | 3/1997 | (WO) | A61K/7/50 |
| WO 97/09957 | 3/1997 | (WO) | A61K/7/00 |
| WO 97/14406 | 4/1997 | (WO) | A61K/7/50 |
| WO 97/16066 | 5/1997 | (WO) | A01N/25/04 |
| WO 97/16168 | 5/1997 | (WO) | A61K/7/50 |
| WO/PCT18447 * | 5/1998 | (WO) | |
| WO 98/18445 | 5/1998 | (WO) | A61K/7/50 |

OTHER PUBLICATIONS

Drug Facts and Comparisons, Wolters Kluwer Publishing Co. pp. 2429, 2431, 2581, 2584, 2586, 1994.*

Ananthapadmanabhan, K.P., Yu, K.K., Meyers, C.L. and Aronson, M.P., Binding of Surfactants to Stratum Corneum, (1996), *J. Soc. Cosmet. Chem.*, vol. 47, pp. 185–200.

Antoine, J.L., Contreras, J.L. and Van Neste, D.J., pH Influence of Surfactant–induced Skin Irritation, (1989), *Dermatosen 37*, pp. 96–100.

Axe, Douglas D. and Bailey, James E., Transport of Lactate and Acetate Through the Energized Cytoplasmic Membrane of *Escherichia coli*, (1995), *Biotechnology and Bioengineering*, vol. 47, pp. 8–19.

Baker, Zelma, Ph.D., Harrison, R.W., Ph.D., and Miller, Benjamin F., M.D., Action of Synthetic Detergents on the Metabolism of Bacteria, (1940), *The Journal of Exp. Med.*, 73, pp. 249–271.

Bandelin, Fred J., The Effect of pH on the Efficiency of Various Mold Inhibiting Compounds, (1958), *The Journal of the American Pharmaceutical Association*, vol. XLVII, No. 10, pp. 96–98.

Bender, Max, Interfacial Phenomenia in Biological Systems, (1991), pp. 1–49.

Blank, Irvin H., PhD, Measurement of pH of the Skin Surface, (1939), *The Journal of Investigatvie Dermatology*, vol. 2, pp. 75–79.

(List continued on next page.)

Primary Examiner—Frederick Krass
Assistant Examiner—Donna Jagoe
(74) Attorney, Agent, or Firm—Stephen T. Murphy; Tara M. Rosnell

(57) ABSTRACT

The present invention relates to an antimicrobial wipe effective against Gram positive bacteria, Gram negative bacteria, fungi, yeasts, molds, and viruses comprising a porous or absorbent sheet impregnated with an antimicrobial cleansing composition, wherein the antimicrobial cleansing composition comprises from about 0.001% to about 5.0%, by weight of the antimicrobial cleansing composition, of an antimicrobial active; from about 0.05% to about 10%, by weight of the antimicrobial cleansing composition, of an anionic surfactant; from about 0.1% to about 10%, by weight of the antimicrobial cleansing composition, of a proton donating agent; and from about 3% to about 99.85%, by weight of the antimicrobial cleansing composition, water; wherein the composition is adjusted to a pH of from about 3.0 to about 6.0; wherein the antimicrobial cleansing composition an One-wash Immediate Germ Reduction Index of greater than about 1.3; and wherein the rinse-off antimicrobial cleansing composition has a Mildness Index of greater than 0.3. The present invention also relates to methods for removing germs from the skin using the antimicrobial wipes described herein.

24 Claims, No Drawings

U.S. PATENT DOCUMENTS

| | | | |
|---|---|---|---|
| 3,256,200 | 6/1966 | Reller et al. | 252/106 |
| 3,326,808 | 6/1967 | Noseworthy | 252/106 |
| 3,398,826 | 8/1968 | Clancy | 206/46 |
| 3,563,371 | 2/1971 | Heinz | 206/46 |
| 3,650,964 | 3/1972 | Sedliar et al. | 252/106 |
| 3,835,057 | 9/1974 | Cheng et al. | 252/107 |
| 3,867,300 | 2/1975 | Karabinos et al. | 252/106 |
| 3,881,210 | 5/1975 | Drach et al. | 15/104.93 |
| 3,969,258 | 7/1976 | Carandang et al. | 252/106 |
| 4,045,364 | 8/1977 | Richter | 252/106 |
| 4,062,976 | 12/1977 | Michaels | 424/319 |
| 4,067,997 | 1/1978 | Kabara | 424/312 |
| 4,075,350 | 2/1978 | Michaels | 424/316 |
| 4,105,783 | 8/1978 | Yu et al. | 424/283 |
| 4,107,328 | 8/1978 | Michaels | 424/316 |
| 4,118,332 | 10/1978 | Apostolatos et al. | 252/107 |
| 4,183,952 | 1/1980 | Michaels | 424/320 |
| 4,404,040 | 9/1983 | Wang | 134/22.14 |
| 4,406,884 | 9/1983 | Fawzi et al. | 424/81 |
| 4,512,987 | 4/1985 | Schindlery | 514/171 |
| 4,514,385 | 4/1985 | Damani et al. | 424/81 |
| 4,518,593 | 5/1985 | Juvin et al. | 424/195 |
| 4,715,980 | 12/1987 | Lopes et al. | 252/106 |
| 4,732,756 | 3/1988 | Johnson et al. | 428/74 |
| 4,732,797 | 3/1988 | Johnson et al. | 428/74 |
| 4,781,974 | 11/1988 | Bouchette et al. | 428/288 |
| 4,820,698 | 4/1989 | Degenhardt et al. | 514/102 |
| 4,822,604 | 4/1989 | Knoll et al. | 424/70 |
| 4,847,072 | 7/1989 | Bissett et al. | 424/59 |
| 4,891,227 | 1/1990 | Thaman et al. | 424/443 |
| 4,891,228 | 1/1990 | Thaman et al. | 424/443 |
| 4,942,029 | 7/1990 | Scheps | 424/78 |
| 4,971,784 | 11/1990 | Holzel et al. | 424/70 |
| 4,975,217 | 12/1990 | Brown-Skrobot et al. | 252/107 |
| 5,143,720 | 9/1992 | Lopes | 424/55 |
| 5,219,887 | 6/1993 | Andrews et al. | 514/552 |
| 5,234,719 | 8/1993 | Richter et al. | 427/384 |
| 5,280,042 | 1/1994 | Lopes | 514/557 |
| 5,378,731 | 1/1995 | Andrews et al. | 514/552 |
| 5,380,756 | 1/1995 | Andrews et al. | 514/552 |
| 5,389,676 | 2/1995 | Michaels | 514/556 |
| 5,441,742 | 8/1995 | Autant et al. | 424/405 |
| 5,480,633 | 1/1996 | Simion et al. | 424/70.1 |
| 5,510,120 * | 4/1996 | Jones et al. | 424/499 |
| 5,512,200 | 4/1996 | Garcia | 252/142 |
| 5,547,988 | 8/1996 | Yu et al. | 514/557 |
| 5,595,984 | 1/1997 | Blank | 514/159 |
| 5,607,980 | 3/1997 | McAtee | 514/476 |
| 5,620,694 | 4/1997 | Girardot | 424/402 |
| 5,629,081 | 5/1997 | Richards et al. | 442/96 |
| 5,631,218 | 5/1997 | Allan et al. | 510/423 |
| 5,635,462 | 6/1997 | Fendler et al. | 510/131 |
| 5,681,802 * | 10/1997 | Fujiwara et al. | 510/130 |
| 5,700,842 | 12/1997 | Cole | 514/721 |
| 5,744,149 | 4/1998 | Girardot | 424/402 |
| 5,780,020 | 7/1998 | Peterson et al. | 424/65 |
| 5,972,361 | 10/1999 | Fowler et al. | |
| 5,980,931 | 11/1999 | Fowler et al. | |
| 6,063,397 | 5/2000 | Fowler et al. | |

OTHER PUBLICATIONS

Brown, M.R.W., The Role of the Cell Envelope in Resistance, *Resistance of Pseudomonas Aeruginosa*, pp. 70–107.

Buckley, D. and Thomas, J., Antimicrobial Activity of Sodium n–Alkylsalicylates, (1971), *Applied Microbiology*, vol. 21, No. 4, pp. 565–568.

Dychdala, G.R. and Lopes, John A., Surface–Active Agents: Acid–Anionic Compounds, *Disinfectants and Antiseptics*: A. By Chemical Type, pp. 256–262.

Flexner, Simon, M.D., Rous, Peyton, M.D., Gasser, Herbert, M.D., The Journal of Experimental Medicine, (1941), V74, pp. 611–620.

Fukahori M., Akatsu S., Sato H., and Yotsuyanagi T., Relationship Between Uptake of p–hydroxybenzoic acid esters by *Escherichia coli* and Antibacterial Activity, (1996), Chem. Pharm. Bull., vol. 44(8), pp. 1567–1570.

Gershenfeld, Louis and Milanick, Vera Elaine, Bactericidal and Bacteriostatic Properties of Surface Tension Depressants, (1941), *American Journal of Pharmaceuticals*, 113, pp. 306–326.

Gershenfeld, Louis, D. Sc. and Perlstein, David, M. Sc., Significance of Hydrogen–ion Concentration in the Evaluation of the Bactericidal Efficiency of Surface Tension Depressants, (1941), *American Journal of Pharmaceuticals*, 113, pp. 89–92.

Gershenfeld, Louis and Witlin, Bernard, Surface Tension Reducents by Bactericidal Solutions: Their In Vitro and In Vivo Efficiencies, (1941), *American Journal of Pharmaceuticals*, 113, pp. 215–236.

Glassman, Harold N., Surface Active Agents and Their Application in Bacteriology, (1948), *Bacteriological Review*, V. 13, pp. 105–148.

Haque H. and A. D. Russell, Cell Envelopes of Gram Negative Bacteria: Compositions, Response to Chelating Agents and Suscpetibility of Whole Cells to Antibacterial Agents, J. Appl. Bact., (1976), vol. 40, pp. 89–99.

Hotchkiss, Rollin D., The Nature of the Bactericidal Actin of Surface Active Agents, *Annals New York Academy of Sciences*, pp. 479–498.

Hubbard, A.W., Moore, L.J., Clothier, R.H., Sulley, H. and Rollin, K.A., Use of In Vitro Methodology to Predict the Irritancy Potential of Surfactants, (1994), *Toxic. in Vitro*, vol. 8, No. 4, pp. 689–691.

Kabara, Jon J., Structure–function relationships of surfactants as antimicrobial agents, (1978), *Journal of the Society of Cosmetic Chemists*, 29, pp. 733–741.

Kostenbauder, Harry B., Physical Factors Influencing the Activity of Antimicrobial Agents, pp. 59–71.

McDade, Joseph J. and Hall, Lawrence B., Survival of Gram–Negative Bacterial in the Environment, (1964), *Am. J. Hyg*, vol. 80, pp. 192–204.

Meincke, B.E., Kranz, R.G., Lynch, D.L., Effect of Irgasan on Bacterial Growth and Its Absorption Into the Cell Wall, (1980), *Microbios*, 28, pp. 133–147.

Ordal, E.J. and Deromedi, F., Studies on the Action of Wetting Agents on Microorganisms, (1943), *Journal of Applied Bacteriology* 45, pp. 293–299.

Rahn, Otto and Conn, Jean E., Effect of Increase in Acidity on Antiseptic Efficiency, (1944), *Industrial Engineering/Chemistry*, Soc. 36 (2) pp. 185–187.

Regos, J., Zak, O., Solf, R., Vischer, W.A. and Weirich, E.G., Antimicrobial Spectrum of Triclosan, a Broad–Spectrum Antimicrobial Agent for Topical Application, (1979), *Dermatologica* 158, pp. 72–29.

Russell, James B., Resistance of *Streptococcus bovis* to Acetic Acid at Low pH: Relationship between intracellular pH and Anion Accumulation, (1991), *Applied and Environmental Microbiology*, vol. 57. No. 1, pp. 255–259.

Russell, J.B., Another explanation for the toxicity of fermentation acids at low pH: anion accumulation versus uncoupling, (1992), *Journal of Applied Bacteriology*, 73, pp. 363–370.

Scalzo, Marcello, Orlandi, Clelia, Simonetti, Nicola and Cerreto, Felice, Study of Interaction Effects of Polyacrylic Acid Polymers (Carbolpol 940) on Antimicrobial Activity of Methyl Parahyroxybenzoate Against Some Gram–negative, Gram–positive Bacteria and Yeast, (1996), *J. Pharm. Pharmacol*, pp. 1201–1205.

Schoenberg, Tom, Formulating Mild Body Washes, (1996), *happi*, pp. 53–56.

Sheena, A.Z. and Stiles, M.E., Immediate and Residual (Substantive) Efficacy of Germicidal Hand Wash Agents, (1983), *Journal of Food Protection*, vol. 46, No. 7, pp. 629–636.

Stotts, Jane, M.S. and Kooistra, John A., Ph.D., Micrococcaceae of Normal Human Skin Before and After Use of an Antibacterial Soap, (1970).

Wortzman, Mitchell S., PhD, Evaluation of Mild Skin Cleansers, (1991), *Dermatologic Clinics*, vol. 9, No. 1, pp. 35–44.

Young, K.M. and Foegeding, Peggy M., Acetic, latic and citric acids and pH inhibitio of *Listeria monocytogenes* Scott A and the Effect on Intracellular pH, (1993), *Journal of Applied Bacteriology*, 74, pp. 515–520.

Ciba Giegy Trade Literature: Basic Formulation for Hand Disinfection 89/42/01, 89/42/05, & 91/01/49.

Head & Shoulders D Product: Finished Product Standard No. 8427 & 8428 dated Dec. 20, 1991.

Oil of Olay Age defying Series Daily Renewal Cleanser with Gentle Microbeads (Copy of Product).

Fowler et al, U.S. Patent Application Serial No. 09/065,991 claims.

U.S. application No. 08/529,258, Glenn et al., filed Sep. 15, 1995.

U.S. application No. 08/959,969, Glenn et al., filed Oct. 24, 1997.

U.S. application No. 08/868,783, Beerse et al., filed Jun. 4, 1997.

U.S. application No. 08/868.695, Beerse et al., filed Jun. 4, 1997.

U.S. application No. 08/969,049, Beerse et al., filed Nov. 12, 1997.

U.S. application No. 08/868,982, Beerse et al., filed Jun. 4, 1997.

U.S. application No. 08/869,302, Beerse et al., filed Jun. 4, 1997.

U.S. application No. 08/869,300, Beerse et al., filed Jun. 4, 1997.

U.S. application No. 08/869,071, Beerse et al., filed Jun. 4, 1997

U.S. application No. 08/869,116, Beerse et al., filed Jun. 4, 1997.

U.S. application No. 08/869,688, Beerse et al., filed Jun. 4, 1997.

U.S. application No. 08/969,057, Beerse et al., filed Nov. 12, 1997.

U.S. application No. 08/868,717, Beerse et al., filed Jun. 4, 1997.

U.S. application No. 08/869,301, Beerse et al., filed Jun. 4, 1997.

U.S. application No. 08/868,718, Beerse et al., filed Jun. 4, 1997.

U.S. application No. 08/967,972, Beerse et al., filed Nov. 12, 1997.

U.S. application No. 08/869,303, Beerse et al., filed Jun. 4, 1997.

U.S. application No. 08/869,129, Beerse et al., filed Jun. 4, 1997.

U.S. application No. 08/869,304, Beerse et al., filed Jun. 4, 1997.

U.S. application No. 08/969,077, Beerse et al., filed Nov. 12, 1997.

U.S. application No. 08/869,117, Beerse et al., filed Jun. 4, 1997.

\* cited by examiner

ANTIMICROBIAL WIPES WHICH PROVIDE IMPROVED IMMEDIATE GERM REDUCTION

TECHNICAL FIELD

The present invention relates to cleansing wipes comprising absorbent sheets impregnated with antimicrobial cleansing compositions. These cleansing wipes provide enhanced antimicrobial effectiveness compared to prior art compositions. Specifically, the cleansing wipe personal cleansing compositions of the invention provide previously unseen immediate germ reduction.

BACKGROUND OF THE INVENTION

Human health is impacted by many microbial entities. Inoculation by viruses and bacteria cause a wide variety of sicknesses and ailments. Media attention to cases of food poisoning, strep infections, and the like is increasing public awareness of microbial issues.

It is well known that the washing of hard surfaces, food (e.g. fruit or vegetables) and skin, especially the hands, with antimicrobial or non-medicated soap, can remove many viruses and bacteria from the washed surfaces. Removal of the viruses and bacteria is due to the surfactancy of the soap and the mechanical action of the wash procedure. Therefore, it is known and recommended that the people wash frequently to reduce the spread of viruses and bacteria.

Bacteria found on the skin can be divided into two groups: resident and transient bacteria. Resident bacteria are Gram positive bacteria which are established as permanent microcolonies on the surface and outermost layers of the skin and play an important, helpful role in preventing the colonization of other, more harmful bacteria and fungi.

Transient bacteria are bacteria which are not part of the normal resident flora of the skin, but can be deposited when airborne contaminated material lands on the skin or when contaminated material is brought into physical contact with it. Transient bacteria are typically divided into two subclasses: Gram positive and Gram negative. Gram positive bacteria include pathogens such as *Staphylococcus aureus*, *Streptococcus pyogenes* and *Clostridium botulinum*. Gram negative bacteria include pathogens such as Salmonella, *Escherichia coli*, Klebsiella, Haemophilus. *Pseudomonas aeruginosa*, Proteus and *Shigella dysenteriae*. Gram negative bacteria are generally distinguished from Gram positive by an additional protective cell membrane which generally results in the Gram negative bacteria being less susceptible to topical antibacterial actives.

Antimicrobial cleansing products have been marketed in a variety of forms for some time. Forms include deodorant soaps, hard surface cleaners, and surgical disinfectants. These traditional rinse-off antimicrobial products have been formulated to provide bacteria reduction during washing. For example, Dial® liquid soaps, when used in hand washing, have been found to reduce the amount of the bacteria on the skin by from about 2.0 log (97%) to about 2.5 log (99.7%) in one 30 second handwash, as measured by standard Health Care Personal Handwash Tests (HCPHWT). That is skin washed with these soaps were contaminated with only 0.3%–3% of the number of bacteria compared to before washing. Antimicrobial liquid cleansers are disclosed in U.S. Pat. No. 4,847,072, Bissett et al., issued Jul. 11, 1989, U.S. Pat. No. 4,939,284, Degenhardt, issued Jul. 3, 1990 and U.S. Pat. No. 4,820,698, Degenhardt, issued Apr. 11, 1989, all of which are incorporated herein by reference.

Some of these antimicrobial products, especially the hard surface cleaners and surgical disinfectants, utilize high levels of alcohol and/or harsh surfactants which have been shown to dry out and irritate skin tissues. Dial® bar soap has been found to provide from 2.5 to 3.0 log reduction in bacteria in one wash, as measured by the HCPHWT. However, Dial® can be drying to the skin with repeated use. Hibiclens® Surgical Scrub provides 2.5 to 3.0 log reduction in germs in one wash, however it utilizes a potent cationic antibacterial agent, chlorohexidine, which has product safety concerns. Ideal personal cleansers should gently cleanse the skin, cause little or no irritation, and not leave the skin overly dry after frequent use and preferably should provide a moisturizing benefit to the skin.

Finally, these traditional antimicrobial compositions have been developed for use in a washing process with water. This limits their use to locations with available water.

Cleansing wipes have been used, in the past, to wash hands and face while traveling or in public or anytime water is not available. In fact, consumers have used absorbent sheets impregnated with topical compositions for a variety of purposes. U.S. Pat. No. 4,045,364, Richter, et al., issued Aug. 30, 1977 teaches a dry disposable paper impregnated with a germicidal composition comprising an anionic surfactant, an elemental iodine or iodophor active ingredient and a weak acid for pH adjustment. The compositions utilize iodine actives which are not stable in the presence of substantial amounts of water and insufficient acid levels to provide the improved immediate germ reduction of the present invention. European Patent Application, EP 0 619 074, Touchet et al., published Oct. 12, 1994, teaches the use of sorbic or benzoic acids as antimicrobial agents in a wipe, however does not teach the anionic surfactant and separate antimicrobial active necessary to achieve the residual effectiveness of the present invention. U.S. Pat. No. 4,975,217, Brown-Skrobot et al., issued Dec. 4, 1990 teaches the use of anionic surfactants and organic acids on a wipe, however does not teach the use of the active required to provide the improved residual effectiveness benefits.

Currently marketed Nice'n Clean®, Wash'n Dry® and No More Germies® are all antibacterial wipes which utilize harsh cationic surfactants with no additional antibacterial active. These products do not provide the improved immediate germ reduction and are harsh to the skin. Current wipes have been found to give about 1.0 log reduction of germs in One-wash tests.

PCT application WO 92/18100, Keegan et al., published Oct. 29, 1992 and PCT application WO 95/32705, Fujiwara et al., published Dec. 7, 1995 teach non-wipe liquid skin cleansers comprising mild surfactants, antibacterial agents and acidic compounds to buffer the pH which provide improved germ hostility. However, the use of the acid compounds for only pH adjustment therein, results in compositions which do not deliver the undissociated acid required to provide the improved immediate germ reduction of the present invention. This situation is compounded in Keegan and Fujiwara by the preference of mild surfactants, including nonionic surfactants. Neither Keegan nor Fujiwara teach the use of their compositions in a form which can be used without available water, e.g. a wipe.

Hibiclens® Surgical Scrub provides 2.5 to 3.0 log reduction in germs in one wash, and U.S. Pat. No. 3,141,821, issued to Compeau Jul. 21, 1964; Irgasan DP 300 (Triclosan) ®) technical literature from Ciba-Giegy, Inc., "Basic Formulation for Hand Disinfection 89/42/01"; Bartzokas, C. A., et al, "Evaluation of the Skin Disinfecting Activity and Cumulative Effect of Chlorhexidine and Triclosan Handwash Preparations on Hands Artificially Contaminated with

*Serratia marcescens*", Infection Control, 1987/Vol. 8, No. 4; all set forth antibacterial skin cleansers compositions which could provide improved immediate germ reduction using certain anionic surfactants, antimicrobial actives and acids. However, the selection, therein, of highly active surfactants or cationic actives with safety issues (i.e. chlorohexidine gluconate) results in personal cleansing compositions which are drying and harsh, or potentially unsafe to use.

Given the health impacts of bacteria like *Staphylococcus aureus, Streptococcus pyogenes* and *Clostridium botulinum*, it would be highly desirable to formulate antimicrobial cleansing products which provides improved immediate germ reduction on the skin, which are mild to the skin and which can be used without water. Existing products have been unable to deliver all of these benefits.

Applicants have found that antimicrobial wipes which provide such mildness and a new level of immediate germ reduction can be formulated by using known porous or absorbent sheets which are impregnated with improved antimicrobial cleansing compositions. These improved antimicrobial cleansing compositions contain antibacterial actives in combination with specific organic and/or inorganic acids as proton donating agents, and specific anionic surfactants, all of which are deposited on the skin. The deposited proton donating agent and anionic surfactant enhance the selected active, to provide a new level of hostility to bacteria contacting the skin.

SUMMARY OF THE INVENTION

The present invention relates to an antimicrobial wipe effective against Gram positive bacteria, Gram negative bacteria, fungi, yeasts, molds, and viruses comprising a porous or absorbent sheet impregnated with an antimicrobial cleansing composition, wherein the antimicrobial cleansing composition comprises from about 0.001% to about 5.0%, by weight of the antimicrobial cleansing composition, of an antimicrobial active; from about 0.05% to about 10%, by weight of the antimicrobial cleansing composition, of an anionic surfactant; from about 0.1% to about 10%, by weight of the antimicrobial cleansing composition, of a proton donating agent; and from about 3% to about 99.85% , by weight of the antimicrobial cleansing composition, water; wherein the composition is adjusted to a pH of from about 3.0 to about 6.0; wherein the antimicrobial cleansing composition an One-wash Immediate Germ Reduction Index of greater than about 1.3; and wherein the antimicrobial wipe has a Mildness Index of greater than 0.3. The present invention also relates to methods for reducing the number of germs on the skin using the antimicrobial wipes described herein.

DETAILED DESCRIPTION OF THE INVENTION

The antimicrobial wipes of the present invention are highly efficacious for providing a improved immediate germ reduction on the skin, are mild to the skin and can be used without additional available water.

The term "antimicrobial wipe" is used herein to mean products in which a sheet of porous or absorbent material have been impregnated with an antimicrobial cleansing composition for the purpose of rubbing the wipe product over a surface to clean the surface and control the growth and viability of transient bacteria. The term "antimicrobial cleansing composition" as used herein means a composition suitable for application to the human skin for the purpose of removing dirt, oil and the like, which additionally controls the growth and viability of transient bacteria on the skin.

The compositions of the present invention can also be useful for treatment of acne. As used herein "treating acne" means preventing, retarding and/or arresting the process of acne formation in mammalian skin.

The compositions of the invention can also be useful for providing an essentially immediate (i.e., acute) visual improvement in skin appearance following application of the composition to the skin. More particularly, the compositions of the present invention are useful for regulating skin condition, including regulating visible and/or tactile discontinuities in skin, including but not limited to visible and/or tactile discontinuities in skin texture and/or color, more especially discontinuities associated with skin aging. Such discontinuities may be induced or caused by internal and/or external factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin.

Regulating skin condition includes prophylactically and/ or therapeutically regulating skin condition. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, such discontinuities. Regulating skin condition involves improving skin appearance and/or feel, e.g., providing a smoother, more even appearance and/or feel. As used herein, regulating skin condition includes regulating signs of aging. "Regulating signs of skin aging" includes prophylactically regulating and/or therapeutically regulating one or more of such signs (similarly, regulating a given sign of skin aging, e.g., lines, wrinkles or pores, includes prophylactically regulating and/ or therapeutically regulating that sign).

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eve area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

The antimicrobial wipes of the present invention comprise the following essential components.

A. THE POROUS OR ABSORBENT SHEET

The antimicrobial cleansing composition is impregnated at the desired weight onto one or both sides of an absorbent sheet (hereinafter sometimes referred to as "substrate") which may be formed from any woven or nonwoven fiber, fiber mixture or foam of sufficient wet strength and absorbency to hold an effective amount of the antimicrobial cleansing composition. It is preferred from the standpoint of antimicrobial effectiveness and mildness to employ substrates with a high absorbent capacity (e.g., from about 5 to about 20 grams/gram, preferably from about 9 to about 20 grams/gram). The absorbent capacity of a substrate is the ability of the substrate, while supported horizontally, to hold liquid. The absorbent capacity of a substrate is measured according to the Absorbent Capacity Method set forth hereinafter in the Analytical Methods section.

In particular, woven or nonwoven fabrics derived from "oriented" or carded fibrous webs composed of textile-length fibers, the major proportion of which are oriented predominantly in one direction are suitable for use herein. These fabrics can be in the form of, for example, wipes or towelettes, including baby wipes and the like.

Methods of making woven and nonwoven cloths are not a part of this invention and, being well known in the art, are not described in detail herein. Generally, however, such cloths are made by air- or water-laying processes in which the fibers or filaments are first cut to desired lengths from long strands, passed into a water or air stream, and then deposited onto a screen through which the fiber-laden air or water is passed. The deposited fibers or filaments are then adhesively bonded together, and otherwise treated as desired to form the woven, nonwoven, or cellulose cloth.

Thermocarded nonwoven cloths (whether or not resin-containing) are made of polyesters, polyamides, or other thermoplastic fibers which can be spand bonded, i.e., the fibers are spun out onto a flat surface and bonded (melted) together by heat or chemical reactions.

The nonwoven cloth substrates used in the invention herein are generally adhesively bonded fibers or filamentous products having a web or carded fiber structure (when the fiber strength is suitable to allow carding) or comprising fibrous mats in which the fibers or filaments are distributed haphazardly or in random array (i.e., an array of fibers in a carded web where partial orientation of the fibers is frequently present, as well as a completely haphazard distributional orientation), or substantially aligned. The fibers or filaments can be natural (e.g., wool, silk, jute, hemp, cotton, linen, sisal, or ramie) or synthetic (e.g., rayon, cellulose ester, polyvinyl derivatives, polyolethins, polyamides, or polyesters) as have been described hereinabove. These nonwoven materials are generally described in Riedel "Nonwoven Bonding Methods and Materials", *Nonwoven World*, (1987).

The absorbent properties preferred herein are particularly easy to obtain with nonwoven cloths and are provided merely by building up the thickness of the cloth, i.e., by superimposing a plurality of carded webs or mats to a thickness adequate to obtain the necessary absorbent properties, or by allowing a sufficient thickness of the fibers to deposit on the screen. Any denier of the fiber (generally up to about 15 denier) can be used, inasmuch as it is the free space between each fiber that makes the thickness of the cloth directly related to the absorbent capacity of the cloth. Thus, any thickness necessary to obtain the required absorbent capacity can be used.

B. THE ANTIMICROBIAL CLEANSING COMPOSITION

The absorbent sheets used in the present invention are impregnated with an antimicrobial cleansing composition. The term "antimicrobial cleansing composition" as used herein means a composition suitable for application to a surface for the purpose of removing dirt, oil and the like which additionally reduces the number of germs on the surface. The compositions, herein, are effective against Gram positive bacteria, Gram negative bacteria, fungi, yeasts, molds, and viruses. Preferred embodiments of the present invention are cleansing compositions suitable for use on the human skin.

I. INGREDIENTS

The antimicrobial cleansing compositions of the wipes of the present invention comprise an antimicrobial active, an anionic surfactant, and a proton donating agent. These components are selected so that the efficacy and optional mildness requirements hereinafter defined for the compositions herein are met. The selection of each component is necessarily dependent on the selection of each of the other components. For example, if a weak acid is selected as the proton donating agent, then in order to realize an efficacious composition, either a more biologically active (but possibly less mild) surfactant must be employed, and/or a high level of acid within the prescribed range must be used and/or a particularly efficacious active must be employed. Similarly, if a mild, but nonefficacious surfactant is employed, then a stronger acid and/or a high level of acid may be necessary to realize an efficacious composition. If a harsh surfactant is utilized, then a mildness agent may have to be utilized. Guidelines for the selection of the individual components are provided herein.

The Antimicrobial Active

The antimicrobial cleansing composition of the antimicrobial wipes of the present invention comprises from about 0.001% to about 5%, preferably from about 0.05% to about 1%, more preferably from about 0.05% to about 0.5% and more preferably from about 0.1% to about 0.25%, by weight of the antimicrobial cleansing composition, of an antimicrobial active. The exact amount of antibacterial active to be used in the compositions will depend on the particular active utilized since actives vary in potency. Non-cationic actives are required in order to avoid interaction with the anionic surfactants of the invention.

Given below are examples of non-cationic antimicrobial agents which are useful in the present invention.

Pyrithiones, especially the zinc complex (ZPT)
Octopirox®
Dimethyldimethylol Hydantoin (Glydant®)
Methylchloroisothiazol inone/methyl isothiazolinone (Kathon CG®)
Sodium Sulfite
Sodium Bisulfite
Imidazolidinyl Urea (Germall 115®)
Diazolidinyl Urea (Germaill II®)
Benzyl Alcohol
2-Bromo-2-nitropropane-1,3-diol (Bronopol®)
Formalin (formaldehyde)
Iodopropenyl Butylcarbamate (Polyphase P100®)
Chloroacetamide
Methanamine
Methyldibromonitrile Glutaronitrile (1,2-Dibromo-2,4-dicyanobutane or Tektamer®)

Glutaraldehyde
5-bromo-5-nitro-1,3-dioxane (Bronidox®)
Phenethyl Alcohol
o-Phenylphenol/sodium o-phenylphenol
Sodium Hydroxymethylglycinate (Suttocide A®)
Polymethoxy Bicyclic Oxazolidine (Nuosept C®)
Dimethoxane
Thimersal
Dichlorobenzyl Alcohol
Captan
Chlorphenenesin
Dichlorophene
Chlorbutanol
Glyceryl Laurate
Halogenated Diphenyl Ethers
    2,4,4'-trichloro-2'-hydroxy-diphenyl ether (Triclosan® or TCS)
    2,2'-dihydroxy-5,5'-dibromo-diphenyl ether
Phenolic Compounds
    Phenol
    2-Methyl Phenol
    3-Methyl Phenol
    4-Methyl Phenol
    4-Ethyl Phenol
    2,4-Dimethyl Phenol
    2,5-Dimethyl Phenol
    3,4-Dimethyl Phenol
    2,6-Dimethyl Phenol
    4-n-Propyl Phenol
    4-n-Butyl Phenol
    4-n-Amyl Phenol
    4-tert-Amyl Phenol
    4-n-Hexyl Phenol
    4-n-Heptyl Phenol
Mono- and Poly-Alkyl and Aromatic Halophenols
    p-Chlorophenol
    Methyl p-Chlorophenol
    Ethyl p-Chlorophenol
    n-Propyl p-Chlorophenol
    n-Butyl p-Chlorophenol
    n-Amyl p-Chlorophenol
    sec-Amyl p-Chlorophenol
    n-Hexyl p-Chlorophenol
    Cyclohexyl p-Chlorophenol
    n-Heptyl p-Chlorophenol
    n-Octyl p-Chlorophenol
    o-Chlorophenol
    Methyl o-Chlorophenol
    Ethyl o-Chlorophenol
    n-Propyl o-Chlorophenol
    n-Butyl o-Chlorophenol
    n-Amyl o-Chlorophenol
    tert-Amyl o-Chlorophenol
    n-Hexyl o-Chlorophenol
    n-Heptyl o-Chlorophenol
    o-Benzyl p-Chlorophenol
    o-Benxyl-m-methyl p-Chlorophenol
    o-Benzyl-m, m-dimethyl p-Chlorophenol
    o-Phenylethyl p-Chlorophenol
    o-Phenylethyl-m-methyl p-Chlorophenol
    3-Methyl p-Chlorophenol
    3,5-Dimethyl p-Chlorophenol
    6-Ethyl-3-methyl p-Chlorophenol
    6-n-Propyl-3-methyl p-Chlorophenol
    6-iso-Propyl-3-methyl p-Chlorophenol
    2-Ethyl-3,5-dimethyl p-Chlorophenol
    6-sec-Butyl-3-methyl p-Chlorophenol
    2-iso-Propyl-3,5-dimethyl p-Chlorophenol
    6-Diethylmethyl-3-methyl p-Chlorophenol
    6-iso-Propyl-2-ethyl-3-methyl p-Chlorophenol
    2-sec-Amyl-3,5-dimethyl p-Chlorophenol
    2-Diethylmethyl-3,5-dimethyl p-Chlorophenol
    6-sec-Octyl-3-methyl p-Chlorophenol
    p-Chloro-m-cresol
    p-Bromophenol
    Methyl p-Bromophenol
    Ethyl p-Bromophenol
    n-Propyl p-Bromophenol
    n-Butyl p-Bromophenol
    n-Amyl p-Bromophenol
    sec-Amyl p-Bromophenol
    n-Hexyl p-Bromophenol
    Cyclohexyl p-Bromophenol
    o-Bromophenol
    tert-Amyl o-Bromophenol
    n-Hexyl o-Bromophenol
    n-Propyl-m,m-Dimethyl o-Bromophenol
    2-Phenyl Phenol
    4-Chloro-2-methyl phenol
    4-Chloro-3-methyl phenol
    4-Chloro-3,5-dimethyl phenol
    2,4-Dichloro-3,5-dimethylphenol
    3,4,5,6-Terabromo-2-methylphenol
    5-Methyl-2-pentylphenol
    4-Isopropyl-3-methylphenol
    Para-chloro-meta-xylenol (PCMX)
    Chlorothymol
    Phenoxyethanol
    Phenoxyisopropanol
    5-Chloro-2-hydroxydiphenylinethane
Resorcinol and its Derivatives
    Resorcinol
    Methyl Resorcinol
    Ethyl Resorcinol
    n-Propyl Resorcinol
    n-Butyl Resorcinol
    n-Amyl Resorcinol
    n-Hexyl Resorcinol
    n-Heptyl Resorcinol
    n-Octyl Resorcinol
    n-Nonyl Resorcinol
    Phenyl Resorcinol
    Benzyl Resorcinol
    Phenylethyl Resorcinol
    Phenylpropyl Resorcinol
    p-Chlorobenzyl Resorcinol
    5-Chloro 2,4-Dihydroxydiphenyl Methane
    4'-Chloro 2,4-Dihydroxydiphenyl Methane
    5-Bromo 2,4-Dihydroxydiphenyl Methane
    4'-Bromo 2,4-Dihydroxydiphenyl Methane
Bisphenolic Compounds
    2,2'-Methylene bis (4-chlorophenol)
    2,2'-Methylene bis (3,4,6-trichlorophenol)
    2,2'-Methylene bis (4-chloro-6-bromophenol)
    bis (2-hydroxy-3,5-dichlorophenyl) sulphide
    bis (2-hydroxy-5-chlorobenzyl)sulphide
Benzoic Esters (Parabens)
    Methylparaben
    Propylparaben
    Butylparaben Ethylparaben
Isopropylparaben
Isobutylparaben
Benzylparaben
Sodium Methylparaben
Sodium Propylparaben
Halogenated Carbanilides
   3,4,4'-Trichlorocarbanilides (Triclocarban® TCC)
   3-Trifluoromethyl-4,4'-dichlorocarbanilide
   3,3',4-Trichlorocarbanilide Another class of antibacterial agents, which are useful in the present invention, are the so-called "natural" antibacterial actives, referred to as natural essential oils. These actives derive their names from their natural occurrence in plants. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, *Hydastis carradensis, Berberidaceae daceae*, Ratanhiae and *Curcunia longa*. Also included in this class of natural essential oils are the key chemical components of the plant oils which have been found to provide the antimicrobial benefit. These chemicals include, but are not limited to anethol, catechole, camphene, carvacol, eugenol, eucalyptol, ferulic acid, farnesol, hinokitiol, tropolone, limonene, menthol, methyl salicylate, thymol, terpineol, verbenone, berberine, ratanhiae extract, caryophellene oxide, citronellic acid, curcumin, nerolidol and geraniol.

Additional active agents are antibacterial metal salts. This class generally includes salts of metals in groups 3b–7b, 8 and 3a–5a. Specifically are the salts of aluminum, zirconium, zinc, silver, gold, copper, lanthanum, tin, mercury, bismuth, selenium, strontium, scandium, yttrium, cerium, praseodymiun, neodymium, promethum, samarium, europium, gadolinium, terbium, dysprosium, holmium, erbium, thulium, ytterbium, lutetium and mixtures thereof.

Preferred antimicrobial agents for use herein are the broad spectrum actives selected from the group consisting of Triclosan®, Triclocarban®, Octopirox®, PCMX, ZPT, natural essential oils and their key ingredients, and mixtures thereof. The most preferred antimicrobial active for use in the present invention is Triclosan®.

Anionic Surfactant

The antimicrobial cleansing compositions of the present invention comprise from about 0.05% to about 10%, preferably from about 0.1% to about 2%, and more preferably from about 0.2% to about 1%, by weight of the cleansing composition, of an anionic surfactant. Without being limited by theory, it is believed that the anionic surfactant disrupts the lipid in the cell membrane of the bacteria. The particular acid used herein reduces the negative charges on the cell wall of the bacteria, crosses through the cell membrane, weakened by the surfactant, and acidifies the cytoplasm of the bacteria. The antimicrobial active can then pass more easily through the weakened cell wall, and more efficiently poison the bacteria.

Nonlimiting examples of anionic lathering surfactants useful in the compositions of the present invention are disclosed in McCutcheon's, *Detergents and Emulsifiers*, North American edition (1990), published by The Manufacturing Confectioner Publishing Co.; McCutcheon's, *Functional Materials*, North American Edition (1992); and U.S. Pat. No. 3,929,678, to Laughlin et al., issued Dec. 30, 1975, all of which are incorporated by reference.

A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and mixtures thereof. Mixtures of anionic surfactants can be used effectively in the present invention.

Anionic surfactants for use in the cleansing compositions include alkyl and alkyl ether sulfates. These materials have the respective formulae $R^1O$—$SO_3M$ and $R^1(CH_2H_4O)_x$—$O$—$SO_3M$, wherein $R^1$ is a saturated or unsaturated, branched or unbranched alkyl group from about 8 to about 24 carbon atoms, x is 1 to 10, and M is a water-soluble cation such as ammonium, sodium, potassium, magnesium, triethanolamine, diethanolamine and monoethanolamine. The alkyl sulfates are typically made by the sulfation of monohydric alcohols (having from about 8 to about 24 carbon atoms) using sulfur trioxide or other known sulfation technique. The alkyl ether sulfates are typically made as condensation products of ethylene oxide and monohydric alcohols (having from about 8 to about 24 carbon atoms) and then sulfated. These alcohols can be derived from fats, e.g., coconut oil or tallow, or can be synthetic. Specific examples of alkyl sulfates which may be used in the cleanser compositions are sodium, ammonium, potassium, magnesium, or TEA salts of lauryl or myristyl sulfate. Examples of alkyl ether sulfates which may be used include ammonium, sodium, magnesium, or TEA laureth-3 sulfate.

Another suitable class of anionic surfactants are the sulfated monoglycerides of the form $R^1CO$—$O$—$CH_2$—$C(OH)H$—$CH_2$—$O$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the form $R^1SO_3M$, wherein $R^1$ is a mono-olefin having from about 12 to about 24 carbon atoms, and M is a water-soluble cation such as ammonium, sodium, potassium, magnesium, triethanolamine, diethanolamine and monoethanolamine. These compounds can be produced by the sulfonation of alpha olefins by means of uncomplexed sulfur trioxide, followed by neutralization of the acid reaction mixture in conditions such that any sultones which have been formed in the reaction are hydrolyzed to give the corresponding hydroxyalkanesulfonate. An example of a sulfonated olefin is sodium $C_{14}/C_{16}$ alpha olefin sulfonate.

Other suitable anionic surfactants are the linear alkylbenzene sulfonates of the form $R^{1-}$—$C_6H_4$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Still other anionic surfactants suitable for this cleansing composition include the primary or secondary alkane sulfonates of the form $R^1SO_3M$, wherein $R^1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method. The sulfonation can occur in either the secondary or primary positions of the alkyl chain. An example of an alkane sulfonate useful herein is alkali metal or ammonium $C_{13}$–$C_{17}$ paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates which are based on taurine, which is also known as 2-aminoethanesulfonic acid. Examples of taurates include N-alkyltaurines such as the one prepared by reacting dodecylamine with sodium isethionate according to the teaching of U.S. Pat. No. 2,658,072 which is incorporated herein by reference in its entirety. Other examples based of taurine include the acyl taurines formed by the reaction of n-methyl taurine with fatty acids (having from about 8 to about 24 carbon atoms).

Another class of anionic surfactants suitable for use in the cleansing composition are the acyl isethionates. The acyl isethionates typically have the formula $R^1CO$—O—$CH_2CH_2SO_3M$ wherein $R^1$ is a saturated or unsaturated, branched or unbranched alkyl group having from about 10 to about 30 carbon atoms, and M is a cation. These are typically formed by the reaction of fatty acids (having from about 8 to about 30 carbon atoms) with an alkali metal isethionate. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form $R^1$—$OCH_2$—$C(OH)H$—$CH_2$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate.

Other suitable anionic surfactants include the sulfonated fatty acids of the form $R^1$—$CH(SO_4)$—COOH and sulfonated methyl esters of the from $R^1$—$CH(SO_4)$—CO—O—$CH_3$, where $R^1$ is a saturated or unsaturated, branched or unbranched alkyl group from about 8 to about 24 carbon atoms. These can be formed by the sulfonation of fatty acids or alkyl methyl esters (having from about 8 to about 24 carbon atoms) with sulfur trioxide or by another known sulfonation technique. Examples include alpha sulphonated coconut fatty acid and lauryl methyl ester.

Other anionic materials include phosphates such as monoalkyl, dialkyl, and trialkylphosphate salts formed by the reaction of phosphorous pentoxide with monohydric branched or unbranched alcohols having from about 8 to about 24 carbon atoms. These could also be formed by other known phosphation methods. An example from this class of surfactants is sodium mono or dilaurylphosphate.

Other anionic materials include acyl glutamates corresponding to the formula $R^1CO$—N(COOH)—$CH_2CH_2$—$CO_2M$ wherein $R^1$ is a saturated or unsaturated, branched or unbranched alkyl or alkenyl group of about 8 to about 24 carbon atoms, and M is a water-soluble cation. Nonlimiting examples of which include sodium lauroyl glutamate and sodium cocoyl glutamate.

Other anionic materials include alkanoyl sarcosinates corresponding to the formula $R^1CON(CH_3)$—$CH_2CH_2$—$CO_2M$ wherein $R^1$ is a saturated or unsaturated, branched or unbranched alkyl or alkenyl group of about 10 to about 20 carbon atoms, and M is a water-soluble cation. Nonlimiting examples of which include sodium lauroyl sarcosinate, sodium cocoyl sarcosinate, and ammonium lauroyl sarcosinate.

Other anionic materials include alkyl ether carboxylates corresponding to the formula $R^{1-}$—$(OCH_{12}CH_2)_x$—$OCH_2$—$CO_2M$ wherein $R^1$ is a saturated or unsaturated, branched or unbranched alkyl or alkenyl group of about 8 to about 24 carbon atoms, x is 1 to 10, and M is a water-soluble cation. Nonlimiting examples of which include sodium laureth carboxylate.

Other anionic materials include acyl lactylates corresponding to the formula $R^1CO$—[O—$CH(CH_3)$—$CO]_x$—$CO_2M$ wherein $R^1$ is a saturated or unsaturated, branched or unbranched alkyl or alkenyl group of about 8 to about 24 carbon atoms, x is 3, and M is a water-soluble cation. Nonlimiting, examples of which include sodium cocoyl lactylate.

Other anionic materials include the carboxylates, nonlimiting examples of which include sodium lauroyl carboxylate, sodium cocoyl carboxylate, and ammonium lauroyl carboxylate. Anionic flourosurfactants can also be used.

Any counter cation, M, can be used on the anionic surfactant. Preferably the counter cation is selected from the group consisting of sodium, potassium, ammonium, monoethanolamine, diethanolamine, and triethanolamilne. More preferably the counter cation is ammonium.

Two factors must be taken into account when selecting the surfactant or surfactants to be employed in the antibacterial cleansing compositions of the antimicrobial wipes herein: 1) the activity of the surfactant molecule at the cell membrane of the bacteria; and 2) the mildness of the surfactant insofar as it affects the Mildness Index (hereinafter described) for the antibacterial composition.

Biological Activity/Mildness of Surfactant

In general, the higher the biological activity of the surfactant, the more residual effectiveness is provided by the composition comprising the surfactant. Typically, however, the biological activity of a surfactant and the mildness of a surfactant are inversely proportional; the higher the biological activity of the surfactant, the harsher the surfactant and the lower the biological activity of the surfactant, the milder the surfactant. Whether a biologically active, but harsh surfactant or a mild, but biologically inactive surfactant is desired will, of course, depend on (or influence) the selection of the other components.

The biological activity/mildness of a pure surfactant can measured directly via a Microtox Response Test hereinafter described in the Analytical Methods section and can be reported as a Microtox Response Index. By "pure surfactant" it is meant a chemical composition consisting essentially of a singale surfactant entity, wherein the entity has essentially one chain length, head group and salt counter ion. From a standpoint of high biological activity, preferred anionic surfactants of the antimicrobial cleansing compositions of the present invention have a Microtox Response Index of less that about 150, more preferably less than about 100 and most preferably less than about 50. From a standpoint of mildness, preferred anionic surfactants of the antimicrobial cleansing compositions of the present invention have a Microtox Response Index of greater than about 25, more preferably greater than about 50 and most preferably greater than about 100. Surfactants with a Microtox Response Index ranging from about 25 to about 150 are typically moderately biologically active and moderately mild.

For surfactant compositions which are mixtures of surfactants rather than pure surfactants (this includes "commercial grade" surfactants which typically comprise mixtures of entities with different chain lengths and potentially have higher levels of impurities), the Microtox Response Index for any individual surfactant component is not a reliable measurement of biological activity or mildness. In the case of mixtures, the Microtox Index of each individual component can be determined and the weighted average used as the Index for the mixture if all the individual components of the mixture are known. If the individual components of a mixture are not known, then the primary head group and chain lengths of the surfactant mixture are better indicators of biological activity/mildness.

Anionic surfactants or mixtures of surfactants with a chain length primarily in the range of from about 8 to about 24 carbon atoms, preferably primarily from about 10 to about 18 carbon atoms and most preferably primarily from about 12 to about 16 carbon atoms are preferred from the standpoint of high biological activity. As used herein "primarily" means at least about 50%. From a standpoint of mildness, it is preferable to minimize C12.

From the standpoint of biological activity, it is preferred that the head group of the anionic surfactant be less than about 15 Angstroms, preferably less than about 10 Angstroms, and more preferably less than about 7 Angstroms. The "head group" is defined as the hydrophilic portion (non-hydrocarbon) of the anionic surfactant, measured from the first polar atom to the end of the molecule. The head group size is estimated from the Van der Waals radius of the atoms and the configuration of the surfactant molecule. Head groups with sizes less than about 7 Angstroms include sulfates, sulfonates, and phosphates. From the standpoint of mildness, it is preferred that the head group size is greater than about 7 Angstroms, and preferably greater than about 10 Angstroms. Head groups with sizes greater than about 10 Angstroms include ethoxylated sulfates, glyceryl ether sulfonates, and isethionates. It is believed that as the head group size increases, more stearic hindrance at the cell wall prevents disruption by the surfactant and, thus, biological activity is decreased and mildness is increased.

The mildness of a surfactant or mixture of surfactants can also be determined by a number of other known, conventional methods for measuring surfactant mildness. For example, the Barrier Destruction Test set forth in T. J. Franz, J. Invest. Dermatol., 1975, 64, pp. 190–195 and in U.S. Pat. No. 4,673,525 to Small et al; issued Jun. 16, 1987, both of which are herein incorporated by reference, is a way of measuring mildness of surfactants. In general, the milder the surfactant, the less skin barrier that is destroyed in the barrier destruction test. Skin barrier destruction is measured by relative amount of radiolabeled water which passes from the test solution through the skin epidermis into the physiological buffer contained in the diffusate chamber. Surfactants having a Relative Skin Barrier Penetration Value of as close to zero as possible up to about 75 are considered mild for purposes herein. Surfactants having a Relative Skin Barrier Penetration Value of greater than about 75 are considered harsh for purposes herein.

In order for the antimicrobial composition of the antimicrobial wipes herein to be effective, both the biological activity of the surfactant and the mildness of the surfactant and acid employed in the composition must be taken into account.

For example, ammonium lauryl sulfate, ALS, is very biologically active (Microtox Index=1.0). Compositions comprising ALS are capable of providing very effective residual antibacterial effectiveness due to its activity, even with lower levels of antibacterial active and proton donating agent. However, compositions containing ALS may require the addition of co-surfactants or polymers, described herein in the Optional Ingredient Section, to achieve most preferred mildness levels for the present invention.

A selection of ammonium laureth-3 sulfate (Microtox= 120) as a surfactant will result in compositions which are very mild, but which would require higher levels of proton donating agent and antimicrobial active in order to achieve the residual effectiveness of the present invention.

Paraffin sulfonate, a commercial grade surfactant sold under the name Hastapur SAS® from Hoechst Celanese, with a small head group and average chain length of 15.5 is a relatively active surfactant. Compositions comprising lower levels of active and acid can be used with higher levels of paraffin sulfonate, where the surfactant provides a larger component of residual effectiveness. Alternately, compositions comprising lower levels of paraffin sulfonate can be combined with even higher levels of active to achieve a mild and effective composition.

Nonlimiting examples of preferred anionic surfactants useful herein include those selected from the group consisting of sodium and ammonium alkyl sulfates and ether sulfates having chain lengths of predominantly 12 and 14 carbon atoms, olefin sulfates having chain lengths of predominantly 14 and 16 carbon atoms, and paraffin sulfonates having chain lengths of from 13 to 17 carbon atoms, and mixtures thereof. Especially preferred for use herein is ammonium and sodium lauryl sulfate, ammonium and sodium myristyl sulfate, ammonium and sodium laureth-1 to laureth-4 sulfate, C14–C16 olefin sulfonates, C13–C17 paraffin sulfonates, and mixtures thereof.

Non-anionic surfactants of the group consisting of nonionic surfactants, cationic surfactants, amphoteric surfactants and mixtures thereof, have been found to actually inhibit residual effectiveness benefits. It is believed that these surfactants interfere with the anionic surfactant disruption of the lipid in the cell membrane. The ratio of the amount of these non-anionic surfactants to the amount of anionic surfactant should be less than about 1:1, preferably less than about 1:2, and more preferably less than about 1:4.

The antimicrobial cleansing compositions of the present invention preferably do not comprise hydrotropic sulfonates, particularly salts of terpenoids, or mono- or binuclear aromatic compounds such as sulfonates of camphor, toluene, xylene, cumene and naphthene.

Proton Donating Agent

The antimicrobial cleansing compositions of the present invention comprise from about 0.1% to about 10%, preferably from about 0.5% to about 8%, more preferably from about 1% to about 5%, based on the weight of the personal cleansing composition, of a proton donating agent. By "proton donating agent" it is meant any acid compound or mixture thereof, which results in undissociated acid on the skin after use. Proton donating agents can be organic acids, including polymeric acids, mineral acids or mixtures thereof.

Organic Acids

Proton donating agents which are organic acids which remain at least partially undissociated in the neat composition and remain so when the compositions are diluted during washing and rinsing. These organic proton donating agents can be added directly to the composition in the acid form or can be formed by adding the conjugate base of the desired acid and a sufficient amount of a separate acid strong enough to form the undissociated acid from the base.

Buffering Capacity

Preferred organic proton donating agents are selected and formulated based on their buffer capacity and pKa. Buffer capacity is defined as the amount of protons (weight %) available in the formulation at the product pH for those acid groups with pKa's less than about 6.0. Buffer capacity can be either calculated using pKa's, pH, and the concentrations of the acids and conjugate bases, ignoring any pKa greater than 6.0, or it can be determined experimentally through a simple acid-base titration using sodium hydroxide or potassium hydroxide using an endpoint of pH equals 6.0.

Preferred organic proton donating agents of the antibacterial cleansing composition herein have a buffer capacity of greater than about 0.005%, more preferably greater than about 0.01%, even more preferably greater than about 0.02%, and most preferably greater than about 0.04%.

Mineral Acids

Proton donating agents which are mineral acids will not remain undissociated in the neat composition and when the compositions are diluted during washing and rinsing. Despite this, it has been found that mineral acids can be effective proton donating agents for use herein. Without being limited by theory, it is believed that the strong mineral acid, acidify the carboxylic and phosphatidyl groups in proteins of the skin cells, thereby providing in-situ undissociated acid. These proton donating agents can only be added directly to the composition in the acid form.

pH

It is critical to achieving the benefits of the invention that the undissociated acid from the proton donating agent (deposited or formed in-situ) remain on the skin in the protonated form. Therefore, the pH of the antimicrobial cleansing compositions of the present invention must be adjusted to a sufficiently low level in order to either form or deposit substantial undissociated acid on the skin. The pH of the compositions should be adjusted and preferably buffered to range from about 3.0 to about 6.0, preferably from about 3.0 to about 5.0 and more preferably from about 3.5 to about 4.5.

A non-exclusive list of examples of organic acids which can be used as the proton donating agent are adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof. A non-exclusive list of examples of mineral acid for use herein are hydrochloric, phosphoric, sulfuric and mixtures thereof.

Water

The antimicrobial cleansing compositions of the present invention comprise from about 3% to about 98.899%, preferably from about 5% to about 98%, more preferably from about 10% to about 97.5%, and most preferably from about 38% to about 95.99% water.

Preferable Optional Ingredients

Mildness Enhancers

In order to achieve the mildness required of the present invention, optional ingredients to enhance the mildness to the skin can be added. These ingredients include cationic and nonionic polymers, co-surfactants, moisturizers and mixtures thereof. Polymers useful herein include polyethylene glycols, polypropylene glycols, hydrolyzed silk proteins, hydrolyzed milk proteins, hydrolyzed keratin proteins, guar hydroxypropyltrimonium chloride, polyquats, silicone polymers and mixtures thereof. When used, the mildness enhancing polymers comprise from about 0.1% to about 1%, preferably from about 0.2% to about 1.0%, and more preferably from about 0.2% to about 0.6%, by weight of the antimicrobial cleansing composition, of the composition. Co-surfactants useful herein include nonionic surfactants such as the Genapol® 24 series of ethoxylated alcohols, POE(20) sorbitan monooleate (Tween® 80), polyethylene glycol cocoate and Pluronic® propylene oxide/ethylene oxide block polymers, and amphoteric surfactants such as alkyl betaines, alkyl sultaines, alkyl amphoacetates, alkyl amphodiacetates, alkyl amphopropionates, and alkyl amphodipropionates. When used, the mildness enhancing co-surfactants comprise from about 20% to about 70%, preferably from about 20% to about 50%, by weight of the anionic surfactant, of the cleansing composition.

Another group of mildness enhancers are lipid skin moisturizing agents which provide a moisturizing benefit to the user of the cleansing wipe when the lipophilic skin moisturizing agent is deposited to the user's skin. When used in the antimicrobial personal cleansing compositions herein, lipophilic skin moisturizing agents are used, they are employed at a level of about 0.1% to about 30%, preferably from about 0.2% to about 10%, most preferably from about 0.5% to about 5% by weight of the composition.

In some cases, the lipophilic skin moisturizing agent can desirably be defined in terms of its solubility parameter, as defined by *Vaughan in Cosmetics and Toiletries*, Vol. 103, p. 47–69, October 1988. A lipophilic skin moisturizing agent having a Vaughan solubility Parameter (VSP) from 5 to 10, preferably from 5.5 to 9 is suitable for use in the antimicrobial cleansing compositions herein.

A wide variety of lipid type materials and mixtures of materials are suitable for use in the antimicrobial cleansing compositions of the present invention. Preferably, the lipophilic skin conditioning agent is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils such as those described in U.S. Pat. No. 3,600,186 to Mattson; Issued Aug. 17, 1971 and U.S. Pat. Nos. 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797,300 to Jandacek; issued Jan. 10, 1989; U.S. Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk tri-glycerides, wax esters, beeswax derivatives, sterols, phospholipids and mixtures thereof. Fatty acids, fatty acid soaps and water soluble polyols are specifically excluded from our definition of a lipophilic skin moisturizing agent.

Hydrocarbon oils and waxes: Some examples are petrolatum, mineral oil microcrystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratio of petrolatum to polybutene ranges from about 90:10 to about 40:60 are also suitable for use as the lipid skin moisturizing agent in the compositions herein.

Silicone Oils: Some examples are dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof. Nonlimiting examples of silicones useful herein are described in U.S. Pat. No. 5,011,681, to Ciotti et al., issued Apr. 30, 1991, which is incorporated by reference.

Di- and tri-glycerides: Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetoelyceride esters are used and an example is acetylated monoglycerides.

Lanolin and its derivatives are preferred and some examples are lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate.

It is most preferred when at least 75% of the lipophilic skin conditioning agent is comprised of lipids selected from the group consisting: petrolatum, blends of petrolatum and high molecular weight polybutene, mineral oil, liquid nondigestible oils (e.g. liquid cottonseed sucrose octaesters) or blends of liquid digestible or nondigestible oils with solid polyol polyesters (e.g. sucrose octaesters prepared from C22 fatty acids) wherein the ratio of liquid digestible or nondigestible oil to solid polyol polyester ranges from about 96:4 to about 80:20, hydrogenated or nonhydrogenated polybutene, microcrystalline wax, polyalkene, paraffin, cerasin, ozokerite, polyethylene, perhydrosqualene; dimetlicones, alkyl siloxane, polymethylsiloxane, methylphenylpolysiloxane and mixtures thereof. When as blend of petrolatum and other lipids is used, the ratio of petrolatum to the other selected lipids (hydrogenated or unhydrogenated polybutene or polydecene or mineral oil) is preferably from about 10:1 to about 1:2, more preferably from about 5:1 to about 1:1.

Stabilizers

When a lipophilic skin moisturizing agent is employed as the mildness enhancer in the antimicrobial compositions herein, a stabilizer may also be included at a level ranging from about 0.1% to about 10%, preferably from about 0.1% to about 8%, more preferably from about 0.1% to about 5% by weight of the antimicrobial cleansing composition.

The stabilizer is used to form a crystalline stabilizing network in the liquid cleansing composition that prevents the lipophilic skin moisturizer agent droplets from coalescing and phase splitting in the product. The network exhibits time dependent recovery of viscosity after shearing (e.g., thixotropy).

The stabilizers used herein are not surfactants. The stabilizers provide improved shelf and stress stability. Some preferred hydroxyl-containing stabilizers include 12-hydroxystearic acid, 9,10-dihydroxystearic acid, tri-9, 10-dihydroxystearin and tri-12-hydroxystearin (hydrogenated castor oil is mostly tri-12-hydroxystearin). Tri-12-hydroxystearin is most preferred for use in the compositions herein. When these crystalline, hydroxyl-containing stabilizers are utilized in the cleansing compositions herein, they are typically present at from about 0.1% to 10%, preferably from 0.1% to 8%, more preferably from 0.1% to about 5% of the antimicrobial cleansing compositions. The stabilizer is insoluble in water under ambient to near ambient conditions.

Alternatively, the stabilizer employed in the cleansing compositions herein can comprise a polymeric thickener. When polymeric thickeners as the stabilizer in the cleansing compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000, anionic, cationic, and nonionic homopolymers derived from acrylic and/or methacrylic acid, anionic, cationic, and nonionic cellulose resins, cationic copolymers of dimethyldialkylammonium chloride, and acrylic acid, cationic homopolymers of dimethylalkylammonium chloride, cationic polyalklene and ethoxypolyalkylene imines, polyethylene glycol of molecular weight from 100,000 to 4,000,000, and mixtures thereof. Preferably, the polymer is selected from the group consisting of sodium polyacrylate, hydroxy ethyl cellulose, cetyl hydroxy ethyl Cellulose, and Polyquaternium 10.

Alternatively, the stabilizer employed in the cleansing compositions herein can comprise C10–C22 ethylene glycol fatty acid esters. C10–C22 ethylene glycol fatty acid esters can also desirably be employed in combination with the polymeric thickeners hereinbefore described. The ester is preferably a diester, more preferably a C14–C18 diester, most preferably ethylene glycol distearate. When C10–C22 ethylene glycol fatty acid esters are utilized as the stabilizer in the personal cleansing compositions herein, they are typically present at from about 3% to about 10%, preferably from about 5% to about 8%, more preferably from about 6% to about 8% of the personal cleansing compositions.

Another class of stabilizer which can be employed in the antimicrobial cleansing compositions of the present invention comprises dispersed amorphous silica selected from the group consisting of fumed silica and precipitated silica and mixtures thereof. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. Precipitated silicas and silica gels are generally made in aqueous solution. See, Cabot Technical Data Pamphlet TD-100 entitled "CAB-O-SIL® Untreated Fumed Silica Properties and Functions", October 1993, and Cabot Technical Data Pamphlet TD-104 entitled "CAB-O-SIL® Fumed Silica in Cosmetic and Personal Care Products", March 1992, both of which are herein incorporated by reference.

The fumed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m./gram, most preferably greater than about 180 sq. m./gram.

When amorphous silicas are used as the stabilizer herein, they are typically included in the cleansing compositions at levels ranging from about 0.1% to about 10%, preferably from about 0.25% to about 8%, more preferably from about 0.5% to about 5%.

A fourth class of stabilizer which can be employed in the antimicrobial cleansing compositions of the present invention comprises dispersed smectite clay selected from the group consisting of bentonite and hectorite and mixtures thereof. Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and flourine. See Merck Index, eleventh Edition, 1989, entry 4538, p. 729, which is herein incorporated by reference.

When smectite clay is employed as the stabilizer in the cleansing compositions of the present invention, it is typically included in amounts ranging from about 0.1% to about 10%, preferably from about 0.25% to about 8%, more preferably from about 0.5% to about 5%.

Other known stabilizers, such as fatty acids and fatty alcohols, can also be employed in the compositions herein. Palmitic acid and lauric acid are especially preferred for use herein.

Other Optional Ingredients

The compositions of the present invention can comprise a wide range of optional ingredients. The *CTFA International Cosmetic Ingredient Dictionary*, Sixth Edition, 1995, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

II. CHARACTERISTICS

The antimicrobial wipes herein, have the following characteristics.

Immediate Germ Reduction Indexes

The antimicrobial wipes provide improved immediate reduction of germs on the skin. The degree of reduction can be measured after one-wash of the In-Vivo Health Care Personal Handwash Test described herein. When measured after one wash (application) the antimicrobial wipe has One-wash Immediate Germ Reduction Index of greater than about 1.3 (95% reduction), preferably greater than about 1.7 (98% reduction), more preferably greater than about 2.0 (99% reduction), and most preferably greater than about 2.3 (99.5% reduction). The index represents a difference in base ten logarithm values of bacterial concentrations between before and after washing. For example, an index of 1.3 represents a reduction in log values of 1.3 ($\Delta$log=1.3) which in turn represents a 95% reduction of bacteria counts.

Mildness Index

The antimicrobial wipes of the present invention comprise a Mildness Index of greater than about 0.3, preferably greater than about 0.4, and more preferably greater than about 0.6. The Mildness Index is measured by the Forearm Controlled Application Test (FCAT) described herein.

III. PREPARATION OF THE ABSORBENT SHEETS IMPREGNATED WITH ANTIMICROBIAL CLEANSING COMPOSITION

Any method suitable for the application of aqueous or aqueous/alcoholic impregnates, including flood coating, spray coating or metered dosing, can be used to impregnate the fibrous webs herein with the antimicrobial cleansing compositions described herein. More specialized techniques, such as Meyer Rod, floating knife or doctor blade, which are typically used to impregnate liquids into absorbent sheets may also be used.

The emulsion should preferably comprise from about 100% to about 400%, preferably from about 200% to about 400% by weight of the absorbent sheet.

After coating, the sheets may be folded into stacks and packaged in any of the moisture and vapor impermeable packages known in the art.

The anti-microbial cleansing compositions of the present invention are made via art recognized techniques for the various forms compositions.

IV. METHODS OF USING THE ANTIMICROBIAL WIPES

The antimicrobial wipe of the present invention are useful for personal cleansing, reducing germs on skin, and providing residual effectiveness Gram negative and Gram positive bacteria, especially on the hands and face. Typically the wipe is used to apply cleansing compositions to the area to be cleansed. The wipes herein can be used for personal cleansing when the use of cleansing products requiring water cannot be, or are inconvenient. Typical quantities of the present wipes useful for cleansing, range from about 1 to about 4 wipes per use, preferably from about 1 to about 2 wipes per use. Typical amounts of antimicrobial cleansing composition used range from about 4 $mg/cm^2$ to about 6 $mg/cm^2$, preferably about 5 $mg/cm^2$ of skin area to be cleansed.

ANALYTICAL TEST METHODS

MICROTOX RESPONSE TEST

Reference: Microtox Manual: A Toxicity Testing Handbook, 1992 Volume I–IV; Microbics Corporation.

Equipment: Microtox M500 Toxicity Testing Unit; Microbics Corporation Connected to computer for data acquisition and analysis according to above reference.

Procedure:

1 Preparation of Sample Stock Solution (Standard Concentration: 1000 ppm)

The stock solution of the test anionic surfactant sample is prepared and used as a stock solution from which all other dilutions are made. The standard "starting concentration", the highest concentration to be tested, is 500 ppm. (If a 500 ppm starting concentration fails to give a calculable result, e.g. an active surfactant kills all reagent at all dilutions, the starting concentration can be adjusted based on a known range of EC50 values of previously tested surfactants.) The stock solution is prepared at two times the starting concentration.

a) Add 0.1 g (or adjusted amount if required) of anionic surfactant, accounting for activity of raw material, to beaker.

b) Microtox Diluent (2% NaCl, Microbics Corp.) is added to total 100 g.

c) Stir solution to make sure of adequate mixing.

2. Reconstitution of Microtox Reagent and Preparation of Assay a) Turn on test unit and allow reagent well temperature to equilibrate at 5.5° C. and incubator block and read well temperature to equilibrate at 15° C.

b) Place a clean cuvette (Microbics Corp.) in the reagent well, and fill with 1.0 ml of Microtox Reconstitution Solution (distilled water, Microbics, Corp.). Allow to cool for 15 minutes.

c) Reconstitute standard vial of Microtox Acute Toxicity Reagent (*Vibrio fischerio*, Microbics Corp.) by quickly adding the 1.0 ml of the cooled reconstitution solution to the reagent vial.

d) Swirl solution in the reagent vial for 2–3 seconds then pour reconstituted reagent back into the cooled cuvette and return the vial to the reagent well. Allow to stabilize for 15 minutes.

e) Place 8 cuvettes containing 500 µl of Microtox Diluent, as assay, into the incubator wells of the test unit. Let cool for 15 minutes.

3. Test Substance Dilution

Prepare 7 serial dilutions of the test substance from the sample stock solution. The final volume of all cuvettes must be 1.0 ml.

a) Place 8 empty cuvettes into a test tube rack.

b) Add 1.0 ml of Microtox Diluent solution to tubes 1–7.

c) Add 2.0 ml of the sample stock solution (1000 ppm) in cuvette 8.

d) Transfer 1.0 ml solution from cuvette 8 to cuvette 7 and mix cuvette 7.

e) Serially transfer 1.0 ml from the newly formed solution to the subsequent cuvette (7 to 6, 6 to 5 etc.). Remove 1.0 ml of solution from cuvette 2 and discard. Cuvette 1 is the blank containing only Microtox Diluent. Place the cuvettes into the test unit incubation wells keeping them in order of lowest to highest concentration. These cuvettes should correspond with the 8 cuvettes prepared in step 2 above. Allow to cool for 15 minutes.

4. Assay and Sample Bioluminescence Testino a) Add 10 µl of reconstituted reagent to the 8 precooled cuvettes of assay prepared in step 2 above (containing 500 µl of diluent). Allow 15 minutes for reagent to stabilize.

b) Start Microtox Data Capture and Reporting Software (Microbics Corp.), select START TESTING, input file name and description, correct starting concentration in ppm (500 if standard concentration is used) and number of controls (1) and dilutions (7). Time 1 should be selected as 5 minutes, time 2 is NONE. Press enter then the space bar to begin testing.

c) Place the assay cuvette containing reagent which corresponds to the test blank into the read well and press SET. After the cuvette has resurfaced press READ and the value will be captured by the computer.

d) Similarly read the remaining 7 cuvettes containing reagent when prompted by the computer by pressing the READ button with the correct cuvette in the READ well.

e) After all 8 initial reading have been taken, transfer 500 µl of the diluted test substance into their corresponding cuvette containing the reagent. Mix by vortexing or swirling and return to the incubation wells. The computer will count for five minutes and prompt you to begin final readings.

f) Take final readings by placing the correct cuvette containing reagent and diluted test surfactant into the read well and pressing READ when prompted by the computer.

5. Data Analysis

The concentration of test substance, in ppm, that decreases the bioluminescence of the Microtox Acute Toxicity Reagent by 50% from the starting value (EC50 Value) can be calculated using the Run Statistics on Data File option of the Microtox Software (recommended) or by conducting a linear regression of the data (% reduction vs. log of concentration). % Reductions are calculated using the following formulas:

$$\frac{\text{Final Reading of Reagent Blank}}{\text{Initial Reading of Reagent Blank}} = \text{Correction Factor}$$

$$\frac{\text{Final Reading of Reagent with Diluted Test Substance}}{\text{Initial Reading of Reagent with Diluted Test Substance}} = \text{Reduction Factor}_x$$

where $x$ means at a corresponding concentration $$\% \text{ Reduction} = \frac{\text{Correction Factor}_x - \text{Reduction Factor}}{\text{Correction Factor}}$$

The Microtox Index is the EC50 value in ppm.

IN-VIVO HEALTH CARE PERSONAL HANDWASH TEST (HCPHWT)

Reference: Annual Book of ASTM Standards Vol. 11.05; ASTM Designation: E 1174–94; "Standard Test Method for Evaluation of Health Care Personnel Handwash Formulation"

1. The test method used is identical to the method explained in this reference with the following changes/clarifications.

a. Testing on a subject was finished after the one wash extraction, when only one-wash data was desired. The test requires at least four subjects to be valid.

b. Historical Data was used as a control in this protocol. (i.e. a control soap was not run in every test)

c. Test Materials

Organism: *Serratia marcescens* ATCC 14756 (incubated 18–24 hrs. at 25 C. in soybean casein broth, adjusted to ~$10^8$ organisms/ml by diluting to 0.45 transmittance with a spectrophotometer)

Dilution Fluid: phosphate buffer (0.1% Triton X-100, 00.3% Lecithin, 1.5% Tween 80) adjusted to pH 7.2 with 1 N HCl Agar: Soybean casein agar with 1.5% polysorbate 80 d. Application Procedure

Laboratory technical places wipe in subject's hand. Subject then wipes his/her entire hand with wipe for fifteen (15) seconds, wiping palm, back of hand, fingers and web areas between fingers, cuticles, and nail beds. Repeat the process for wiping of other hand. Discard wipe. Hands are not dried.

e. Bacteria were enumerated by performing serial dilutions (1:10) of inoculum or extracted samples and spreading 0.1 ml of dilution on plates. Results are reported as the log reduction of bacteria from baseline.

One-wash Immediate Germ Reduction Index=Log (CFU's) in Baseline Extraction−Log (CFU's) in Post−One Wash Extraction Ten-wash Immediate Germ Reduction Index=Log (CFU's) in Baseline Extraction−Log (CFU's) in Post−Ten Wash Extraction f. Hands were decontaminated by submersion in 70% ethanol for 15 sec. and then a five minute wash with control soap and water.

FOREARM CONTROLLED APPLICATION TEST (FCAT)

Reference: Ertel, K. D., et al.; "A Forearm Controlled Application Technique for Estimating the Relative Mildness of Personal Cleansing Products"; J. Soc. Cosmet. Chem. 46 (1995) 67–76.

The Forearm Controlled Application Test, or FCAT, is a comparative test which discriminates differences in product mildness to the skin. A test product is compared to a standard soap based cleansing bar control.

Test Group Restrictions

Test groups of 20–30 subjects, 18 to 55 years of age, who regularly wash with soap are used. Potential subjects who (1) have an initial dryness grade of 3.0 or higher on the forearms as assessed during the initial examination, (2) have skin cancer, eczema, or psoriasis on the forearms, (3) are receiving injectable insulin, (4) are pregnant or lactating, or (5) are receiving treatment for skin problems or contact allergy are excluded. Subjects are to avoid hot tubs, swimming, and sun lamps, and to refrain from applying any soaps, cleansing products, creams, or gels to their forearms for the duration of the study. Subjects are to keep water off their forearms for at least two hours before the grading process. The studies are executed using a blinded, random product order format. Clinical assistant should verify the correct treatment sequence and document such before washing each subject.

Products are applied to the forearms a total of nine (9) times: two (2) times each day on the first four (4) days of the study and one (1) time on the final day. Visits to the test facility for washing must be spaced by a minimum of three (3) hours.

All clinical assistants must wear disposable gloves during wash procedure, rinsing them between treatments, and changing between subjects.

Control Product

The control product is a rolled bar soap containing:

| | |
|---|---|
| 56.1% | Sodium Tallowate |
| 18.7% | Sodium Cocoate |
| 0.7% | Sodium Chloride |
| 24% | Water |
| 0.5% | Minors (Perfume, Impurities) |

Product Application Procedure

Both test and control products are tested on the same arm. The following test procedure is used.

1. The subject wets the entire surface of his/her volar forearm with 95–100° F. tap water by holding the arm briefly under running tap water.

2. A clinical assistant wets one-quarter sheet (approximately 8"×6") of Masslinn® towel with tap water, then squeezes the towel gently to remove excess water.

3. A clinical assistant applies the products to the arm, beginning with the product designated for the site nearest the elbow, using the appropriate procedure as follows:

Liquid Product a. Dispense 0.10 cc of test product from a syringe into the center of the appropriate marked area.

b. Wet two finders of gloved (latex) hand under the running tap (index and middle fingers).

c. Move wetted fingers in a circular motion over the application site for 10 seconds to lather product.

d. Lather remains on the application site for 90 seconds, then is rinsed off with running tap water for 15 seconds, taking care not to wash lather off the adjacent sites. After 10 seconds of the rinse has expired, the Clinical Assistant will gently rub the site being rinsed with her two gloved fingers for the remaining 5 seconds of the rinse.

Bar Product a. Wet two finders of gloved (latex) hand under the running tap (index and middle fingers).

b. Wet bar by holding bar briefly under running tap water. Test bars must be wet under a running tap at the start of each day.

c. Rub wetted fingers in a circular motion, over the surface of the bar, for 15 seconds to form lather on bar and fingers.

d. Rub the lathered fingers on the application site in a circular motion for 10seconds to lather product on the skin.

e. Lather remains on the application site for 90 seconds, then is rinsed off with running tap water for 15 seconds, taking care not to wash lather off the adjacent sites. After 10 seconds of the rinse has expired, the Clinical Assistant will gently rub the site being rinsed with her two gloved fingers for the remaining 5 seconds of the rinse.

Wipe Products a. Fold wipe in half, crosswise, and gently rub the wipe in a curricular motion within the appropriate area.

b. Allow site to air dry for 90 seconds. Do not rinse site.

Leave-on Product a. Dispense 0.10 cc of test product from a syringe into the center of the appropriate marked area.

b. Move gloved fingers in a circular motion over the application site for 10 seconds.

c. Allow site to air dry for 90 seconds. Do not rinse site.

4. While waiting for the 90 second residence time to expire, the above procedure will be repeated on the remaining application site on that arm, working down the arm toward the wrist.

5. Steps 1–4 are repeated on the appropriate test areas so two applications of product are made to test areas.

6. After all of the application areas have two applications of products, the clinical assistant gently pats the subject's arm dry with a disposable paper towel.

Evaluation

The skin on each treatment area is evaluated by an expert grader at baseline and three hours after the final study wash. The treatment areas are evaluated under 2.75×magnification (model KFM-1A Luxo Illuminated Magnifying Lamp, Marshall Industries, Dayton, Ohio) with controlled lighting (General Electric Cool White, 22-watt, 8" Circuline fluorescent bulb).

The skin is evaluated by an expert grader, for dryness and a rating is assigned based on the definitions set forth below.

TABLE 1

Forearm Grading Scale

| Rating | Skin Dryness |
|---|---|
| 0 | No dryness |
| 1.0 | Patches of slight powderiness and occasional patches of small scales may be seen. |
| 2.0 | Generalized slight powderiness. Early cracking or occasional small lifting scales may be present. |
| 3.0 | Generalized moderate powderiness and/or heavy cracking and lifting scales. |
| 4.0 | Generalized heavy powderiness and/or heavy cracking and lifting scales. |
| 5.0 | Generalized high cracking and lifting scales. Eczematous change may be present. Powderiness may be present but not prominent. May see bleeding crack. |
| 6.0 | Generalized severe cracking. Eczematous change may be present. Bleeding cracks may be present. Scales large, may be beginning to disappear. |

The FCAT generally produces only mild to moderate skin irritation; however, if a treated site reaches a rating of 5.0 or greater, at any time during the study, treatment of all sites on that subject should be discontinued.

Data

After all subjects have been evaluated at the end of the test, the following values are determined:

$Rc_o$=The average rating of control product area at baseline $Rc_f$=The average rating of control product area at test end $Rt_o$=The average ratting of test product area at baseline $Rt_f$=The average rating if test product area at test end.

There are many external conditions which could influence the FCAT, such as relative humidity and water softness. The test is valid only if sufficient response is observed in the skin to the control product. The control response must be greater than 1.0 (i.e., $Rc_f - Rc_o \geq 1.0$) for the test to be valid.

Given a valid test, the Mildness Index of the test product is the difference in the skin responses to two products.

Mildness Index=$(Rc_f - Rc_o) - (Rt_f - Rt_o)$

CONSISTENCY (k) AND SHEAR INDEX (n) OF THE LIPOPHILIC SKIN MOISTURIZING AGENT

The Carrimed CSL 100 Controlled Stress Rheometer is used to determine Shear Index, n, and Consistency, k, of the lipophilic skin moisturizing agent used herein. The determination is performed at 35° C. with the 4 cm 2° cone measuring system typically set with a 51 micron gap and is performed via the programmed application of a shear stress (typically from about 0.06 dynes/sq. cm to about 5,000 dynes/sq. cm) over time. If this stress results in a deformation of the sample, i.e. strain of the measuring geometry of at least 10–4 rad/sec, then this rate of strain is reported as a shear rate. These data are used to create a viscosity $\mu$ Vs. shear rate $\gamma'$ flow curve for the material. This flow curve can then be modeled in order to provide a mathematical expression that describes the material's behavior within specific limits of shear stress and shear rate. These results were fitted with the following well accepted power law model (see for instance: *Chemical Engineering*, by Coulson and Richardson, Pergamon, 1982 or *Transport Phenomena* by Bird, Stewart and Lightfoot, Wiley, 1960):

Viscosity, $\mu = k(\gamma')^{n-1}$

VISCOSITY OF THE ANTIMICROBIAL CLEANSING COMPOSITION

The Wells-Brookfield Cone/Plate Model DV-II+ Viscometer is used to determine the viscosity of the antimicrobial cleansing compositions herein. The determination is performed at 25° C. with the 2.4 cm° cone (Spindle CP-41) measuring system with a gap of 0.013 mm between the two small pins on the respective cone and plate. The measurement is performed by injecting 0.5 ml of the sample to be analyzed between the cone and plate and rotating the cone at a set speed of 1 rpm. The resistance to the rotation of the cone produces a torque that is proportional to the shear stress of the liquid sample. The amount of torque is read and computed by the viscometer into absolute centipoise units (mPa's) based on geometric constants of the cone, the rate of rotation, and the stress related torque.

ABSORBENT CAPACITY

Substrate samples are placed in a temperature and relative humidity-controlled location for at least 2 hours prior to testing (temperature=73° F.±2° F., relative humidity 50%±2%).

A full size substrate sheet is supported horizontally in a tared filament lined basket and weighed to provide the weight of the dry sheet. The filament lined basket has crossed filaments which serve to support the sheet horizontally. The crossed filaments permit unrestricted movement of water into and out of the substrate sheet.

The substrate sheet, still supported in the basket, is lowered into a distilled water bath having a temperature of 73° F.±2° F. for one minute. The basket is then raised from the bath and the substrate sheet is allowed to drain for 1 minute. The basket and sheet are then re-weighed to obtain the weight of the water absorbed by the substrate sheet.

The Absorbent Capacity, in grams/gram, is calculated by dividing the weight of the water absorbed by the sheet by the weight of the dry sheet. the Absorbent Capacity is reported as an average of at least 8 measurements.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name.

Fifteen antimicrobial cleansing compositions are prepared according to the tables below.

| Antimicrobial Cleansing Compositions | | | | | |
|---|---|---|---|---|---|
| Component | Ex. 1 | Ex. 2 | Ex. 3 | Ex. 4 | Ex. 5 |
| Mineral oil | 1.00% | 1.00% | 1.00% | 1.00% | 0.00% |
| Propylene glycol | 1.00% | 1.00% | 1.00% | 1.00% | 1.00% |
| Ammonium Lauryl Sulfate | 0.60% | 0.60% | 0.60% | 0.60% | 0.60% |
| Citric Acid | 4.00% | 0.00% | 0.00% | 0.00% | 0.00% |
| Sodium Citrate | 3.30% | 0.00% | 2.00% | 0.00% | 0.00% |

-continued

Antimicrobial Cleansing Compositions

| Component | | | | | |
|---|---|---|---|---|---|
| Succinic Acid | 0.00% | 4.00% | 0.00% | 0.00% | 4.00% |
| Sodium Succinate | 0.00% | 3.30% | 0.00% | 0.00% | 3.20% |
| Malic Acid | 0.00% | 0.00% | 2.50% | 0.00% | 0.00% |
| Malonic Acid | 0.00% | 0.00% | 0.00% | 4.00% | 0.00% |
| Sodium Malonate | 0.00% | 0.00% | 0.00% | 3.20% | 0.00% |
| Steareth 20 | 0.55% | 0.55% | 0.55% | 0.55% | 0.00% |
| Steareth 2 | 0.45% | 0.45% | 0.45% | 0.45% | 0.00% |
| Triclosan ® | 0.15% | 0.15% | 0.15% | 0.15% | 0.15% |
| Miscellaneous | 0.36% | 0.36% | 0.36% | 0.36% | 0.36% |
| Water | q.s. | q.s. | q.s. | q.s. | q.s. |
| pH | 4.0 | 4.5 | 3.9 | 3.9 | 3.9 |
| Microtox of Anionic Surfactant | 1 | 1 | 1 | 1 | 1 |
| Head Group Size of Anionic Surfactant | Small | Small | Small | Small | Small |
| Primary Chain Length of Anionic Surfactant | 12 | 12 | 12 | 12 | 12 |

| Component | Ex. 6 | Ex. 7 | Ex. 8 | Ex. 9 | Ex. 10 |
|---|---|---|---|---|---|
| Mineral oil | 0.00% | 0.00% | 1.00% | 1.00% | 1.00% |
| Propylene glycol | 1.00% | 1.00% | 1.00% | 1.00% | 1.00% |
| Ammonium Lauryl Sulfate | 0.60% | 0.60% | 0.60% | 0.60% | 1.00% |
| Citric Acid | 0.00% | 0.00% | 2.50% | 2.50% | 4.00% |
| Sodium Citrate | 0.00% | 3.70% | 2.00% | 2.00% | 3.20% |
| Succinic Acid | 4.00% | 0.00% | 0.00% | 0.00% | 0.00% |
| Sodium Succinate | 3.00% | 0.00% | 0.00% | 0.00% | 0.00% |
| Malic Acid | 0.00% | 4.00% | 0.00% | 0.00% | 0.00% |
| Steareth 20 | 0.55% | 0.00% | 0.55% | 0.08% | 0.28% |
| Steareth 2 | 0.45% | 0.00% | 0.45% | 0.07% | 0.23% |
| Oleth 20 | 0.00% | 0.00% | 0.00% | 0.08% | 0.28% |
| Oleth 2 | 0.00% | 0.00% | 0.00% | 0.07% | 0.23% |
| Triclosan ® | 0.00% | 0.50% | 0.50% | 0.15% | 0.25% |
| Thymol | 1.00% | 0.00% | 0.00% | 0.00% | 0.00% |
| Miscellaneous | 0.36% | 0.36% | 0.36% | 0.36% | 0.36% |
| Water | q.s. | q.s. | q.s. | q.s. | q.s. |
| pH | 3.2 | 5.0 | 3.9 | 3.9 | 3.9 |
| Microtox of Anionic Surfactant | 1 | 1 | 1 | 1 | |
| Head Group Size of Anionic Surfactant | Small | Small | Small | Small | Small |
| Primary Chain Length of Anionic Surfactant | 12 | 12 | 12 | 12 | 12 |

| Component | Ex. 11 | Ex. 12 | Ex. 13 | Ex. 14 | Ex. 15 |
|---|---|---|---|---|---|
| Mineral oil | 1.00% | 1.00% | 1.00% | 1.00% | 1.00% |
| Propylene glycol | 1.00% | 1.00% | 1.00% | 1.00% | 1.00% |
| Ammonium Lauryl Sulfate | 0.00% | 0.00% | 0.00% | 0.00% | 0.60% |
| Ammonium Laureth Sulfate | 0.00% | 5.00% | 0.00% | 0.00% | 0.00% |
| Hostapur SAS 60 (SPS) | 1.00% | 0.00% | 0.00% | 0.00% | 0.00% |
| $C_{14}$–$C_{16}$ Sodium Alpha Olefin Sulfonate | 0.00% | 0.00% | 2.00% | 0.00% | 0.00% |
| Sodium Lauroyl Sarcosinate | 0.00% | 0.00% | 0.00% | 1.00% | 0.00% |
| Citric Acid | 0.055% | 7.50% | 0.00% | 0.00% | 0.00% |
| Sodium Citrate | 0.00% | 4.00% | 2.00% | 0.00% | 0.00% |
| Succinic Acid | 4.00% | 0.00% | 0.00% | 0.00% | 0.00% |
| Sodium Succinate | 0.67% | 0.00% | 0.00% | 0.00% | 0.00% |
| Malic Acid | 0.00% | 0.00% | 2.50% | 0.00% | 0.00% |
| Malonic Acid | 0.00% | 0.00% | 0.00% | 4.00% | 0.00% |
| Sodium Malonate | 0.00% | 0.00% | 0.00% | 3.20% | 0.00% |
| Salicylic Acid | 0.00% | 0.00% | 0.00% | 0.00% | 0.50% |
| Steareth 20 | 0.55% | 0.55% | 0.55% | 0.55% | 0.55% |
| Steareth 2 | 0.45% | 0.45% | 0.45% | 0.45% | 0.45% |
| Triclosan ® | 0.15% | 3.00% | 0.15% | 0.01% | 0.15% |
| Cocamidopropyl Betaine | 0.00% | 0.00% | 0.00% | 4.00% | 0.00% |
| Polyquat 10 | 0.00% | 0.00% | 0.00% | 0.40% | 0.00% |
| Miscellaneous | 0.36% | 0.36% | 0.36% | 0.36% | 0.36% |
| Water | q.s. | q.s. | q.s. | q.s. | q.s. |
| pH | 3–6 | 3–6 | 3–6 | 3–6 | 3–6 |
| Microtox of Anionic Surfactant | n/a | 150 | 26 | <15 | 1 |
| Head Group Size of Anionic Surfactant | Small | Large | Small | Large | Small |
| Primary Chain Length of Anionic Surfactant | 15.5 | 12 | 14–16 | 12 | 12 |

The antimicrobial cleansing compositions shown all have a One-wash Immediate Germ Reduction Index of greater than about 1.3 and a Mildness Index of greater than 0.3.

Procedure for Making Antimicrobial Cleansing Composition Examples

When mineral oil is used, premix mineral oil, propylene glycol, active, steareth 2 and 20, oleth 2 and 20, and 50%, by weight of the oil, glycol, active, steareth and oleth materials, water to a premix vessel. Heat to 165° F.±10° F. Add additional 50%, by weight of the oil, glycol, active, steareth and oleth materials, of water to the premix tank.

Add all but 5 weight percent of remaining water to second mix tank. If required, add premix to the mix tank. Add surfactants to mix tank. Heat materials to 155° F.±10° F. and mix until dissolved. Cool to less than 100° F., add acid and antibacterial active, if not in premix, and perfumes. Mix until materials are dissolved. Adjust pH to target with required buffer (NaOH or buffer salt). Add remaining water to complete product.

Procedure for Making Antimicrobial Wipe Examples Compositions 1–15 are impregnated onto absorbent sheets as follows:

Composition 1–15 are impregnated onto a wet and air laid woven absorbent sheet comprised of 85% cellulose and 15% polyester at 260% by weight of the absorbent sheet by pouring the composition onto the sheet via a cup.

Composition 1–15 are impregnated onto a wet and air laid woven absorbent sheet comprised of 100% cellulose at 260% by weight of the sheet by pouring the composition onto the sheet via a cup.

Compositions 1–15 are impregnated onto separate wet and air laid nonwoven absorbent sheets comprised of 50% cellulose and 50% polyester at 260% by weight of the sheet by pouring the compositions onto the sheets via a cup.

What is claimed is:

1. An antimicrobial wipe effective against Gram positive bacteria, Gram negative bacteria, fungi, yeasts, molds, and viruses comprising a porous or absorbent sheet impregnated with an antimicrobial cleansing composition, wherein the antimicrobial cleansing composition comprises the following individual components:
   a. from about 0.001% to about 5.0%, by weight of the antimicrobial cleansing composition, of an antimicrobial active;
   b. from about 0.05% to about 10%, by weight of the antimicrobial cleansing composition, of an anionic surfactant;
   c. from about 0.1% to about 10%, by weight of the antimicrobial cleansing composition, of a proton donating agent; and
   d. from about 3% to about 99.85%, by weight of the antimicrobial cleansing composition, water;
   wherein the composition is adjusted to a pH of from about 3.0 to about 6.0;
   wherein the antimicrobial cleansing composition exhibits a One-wash Immediate Germ Reduction Index of greater than about 1.3; and wherein the antimicrobial cleansing composition has a Mildness Index of greater than 0.3.

2. An antimicrobial wipe according to claim 1 wherein the antimicrobial active is selected from the group consisting of triclosan, triclocarban, piroctone olamine, PCMX, ZPT, natural essential oils and their key ingredients, and mixtures thereof.

3. An antimicrobial wipe according to claim 2 wherein the antimicrobial active is triclosan.

4. An antimicrobial wipe according to claim 2 wherein the anionic surfactant has a Microtox Response Index of less than about 150.

5. An antimicrobial wipe according to claim 2 wherein the proton donating agent is an organic acid having a Buffering Capacity of greater than about 0.005.

6. An antimicrobial wipe according to claim 2 wherein the proton donating agent is a mineral acid.

7. An antimicrobial wipe according to claim 5 wherein the composition is adjusted to a pH of from about 3.5 to about 5.0.

8. An antimicrobial wipe according to claim 7 wherein the ratio of the amount of non-anionic surfactants to the amount of anionic surfactant in the antimicrobial cleansing composition is less than 1:1.

9. An antimicrobial wipe effective against Gram positive bacteria, Gram negative bacteria, fungi, yeasts, molds, and viruses comprising a porous or absorbent sheet impregnated with an antimicrobial cleansing composition, wherein the antimicrobial cleansing composition comprises the following individual components:
   a. from about 0.05% to about 1.0%, by weight of the antimicrobial cleansing composition, of an antimicrobial active;
   b. from about 0.1% to about 2%, by weight of the antimicrobial cleansing composition, of an anionic surfactant;
   c. from about 0.5% to about 8%, by weight of the antimicrobial cleansing composition, of a proton donating agent; and
   d. from about 3% to about 99.85%, by weight of the antimicrobial cleansing composition, water;
   wherein the composition is adjusted to a pH of from about 3.0 to about 6.0;
   wherein the antimicrobial cleansing composition exhibits a One-wash Immediate Germ Reduction Index of greater than about 1.7; and wherein the antimicrobial composition has a Mildness Index of greater than 0.4.

10. An antimicrobial wipe according to claim 9 wherein the antimicrobial active is selected from the group consisting of triclosan, triclocarban, piroctone olamine, PCMX, ZPT, natural essential oils and their key ingredients, and mixtures thereof.

11. An antimicrobial wipe according to claim 10 wherein the antimicrobial active is triclosan.

12. An antimicrobial wipe according to claim 10 wherein the anionic surfactant has a Microtox Response Index of less than about 150.

13. An antimicrobial wipe according to claim 10 wherein the proton donating agent is an organic acid having a Buffering Capacity of greater than about 0.005.

14. An antimicrobial wipe according to claim 10 wherein the proton donating agent is a mineral acid.

15. An antimicrobial wipe according to claim 13 wherein the composition is adjusted to a pH of from about 3.5 to about 5.0.

16. An antimicrobial wipe according to claim 15 wherein the ratio of the amount of non-anionic surfactants to the amount of anionic surfactant in the antimicrobial cleansing composition is less than 1:1.

17. An antimicrobial wipe according to claim 16 which further comprises from about 1% to about 30%, by weight of the antimicrobial cleansing composition, of a lipophilic skin moisturizing agent.

18. A method for providing improved immediate reduction of germs on the skin comprising rubbing the antimicrobial wipe of claim 1 on human skin, wherein the antimicrobial cleansing composition is applied to the skin in a safe and effective amount.

19. A method for providing improved immediate reduction of germs on the skin, comprising rubbing the antimicrobial wipe of claim 9 on human skin, wherein the antimicrobial cleansing composition is applied to the skin in a safe and effective amount.

20. A method for treating acne, comprising rubbing the antimicrobial wipe of claim 1 on human skin, wherein the antimicrobial cleansing composition is applied to the skin in a safe and effective amount.

21. An antimicrobial wipe according to claim 1 wherein the antimicrobial cleansing composition comprises from about 0.05% to about 5%, by weight of the antimicrobial cleansing composition, of the anionic surfactant.

22. An antimicrobial wipe according to claim 1 wherein the antimicrobial cleansing composition comprises from about 0.05% to about 2%, by weight of the antimicrobial cleansing composition, of the anionic surfactant.

23. An antimicrobial wipe according to claim 1 wherein the ratio of the amount of non-anionic surfactants to the amount of anionic surfactant in the antimicrobial cleansing composition is less than 1:2.

24. An antimicrobial wipe according to claim 1 wherein the ratio of the amount of non-anionic surfactants to the amount of anionic surfactant in the antimicrobial cleansing composition is less than 1:4.

* * * * *